(12) United States Patent
Cooper

(10) Patent No.: US 8,496,955 B2
(45) Date of Patent: Jul. 30, 2013

(54) CALCIUM PHOSPHATE/SULFATE-BASED BONE IMPLANT COMPOSITION

(75) Inventor: John Joseph Cooper, Crewe (GB)

(73) Assignee: Biocomposites Limited, Staffordshire (GB)

(*) Notice: Subject to any disclaimer, the term of this patent is extended or adjusted under 35 U.S.C. 154(b) by 0 days.

(21) Appl. No.: 13/241,999

(22) Filed: Sep. 23, 2011

(65) Prior Publication Data

US 2012/0045484 A1 Feb. 23, 2012

Related U.S. Application Data

(60) Continuation-in-part of application No. 12/356,357, filed on Jan. 20, 2009, which is a division of application No. 10/476,242, filed as application No. PCT/GB02/01986 on May 1, 2002, now abandoned.

(30) Foreign Application Priority Data

May 2, 2001 (GB) .................................. 0110726.7

(51) Int. Cl.
*A61F 13/00* (2006.01)
*A61F 2/00* (2006.01)

(52) U.S. Cl.
USPC .......................................... 424/423; 424/422

(58) Field of Classification Search
None
See application file for complete search history.

(56) References Cited

U.S. PATENT DOCUMENTS

| | | | |
|---|---|---|---|
| 4,778,471 A | 10/1988 | Bajpai | |
| 5,149,368 A | 9/1992 | Liu et al. | |
| 5,679,723 A | 10/1997 | Cooper et al. | |
| 5,824,087 A | 10/1998 | Aspden et al. | |
| 6,224,635 B1 | 5/2001 | Ricci et al. | |
| 8,003,121 B1 * | 8/2011 | Dingeldein et al. | 424/423 |
| 2001/0032022 A1 | 10/2001 | Ricci et al. | |
| 2004/0151751 A1 | 8/2004 | Cooper | |
| 2009/0124536 A1 | 5/2009 | Coooper | |

FOREIGN PATENT DOCUMENTS

| | | |
|---|---|---|
| EP | 94400608.9 | 9/1994 |
| JP | 3261643 A | 11/1991 |
| JP | 7002691 A | 1/1995 |
| JP | 7008548 A | 1/1995 |
| JP | 2000 159564 A | 6/2000 |
| WO | WO 0209783 A1 * | 2/2002 |
| WO | WO 02/087649 | 11/2002 |
| WO | WO 2011/098438 | 8/2011 |

OTHER PUBLICATIONS

Ohura K et al., Resorption of, and bone formation from, new beta-tricalcium phosphate-monocalcium phosphate cements: an in vivo study, Journal of Biomedical Materials Research. Feb. 1996, 193-200, vol. 30—No. 2, United States.
Pepelassi E M et al., "Doxycycline-tricalcium phosphate composite graft facilitates osseous healing in advanced periodontal furcation defects," Journal of Periodontology. Feb. 1991, 106-115, vol. 62—No. 2, United States.
Ikenaga M et al. Biomechanical characterization of a biodegradable calcium phosphate hydraulic cement: a comparison with porous biphasic Calcium phosphate ceramics, Journal of Biomedical Materials Research. Apr. 1998, 139-144, vol. 40—No. 1, United States.
Ohura K et al., "Healing of segmental bone defects in rats induced by a beta-TCP-MCPM cement combined with rhBMP-2," Journal of Biomedical Materials Research. Feb. 1999, vol. 44—No. 2, United States.
"Zinc Oxide; Toxic Chemical Release Report; Community Right-to-Know", Federal Register Environmental Documents, Sep. 12, 1995, p. 3, Accessed online on Dec. 7, 2007 at http://www.epa.gov/fedrgster/EPA-TRI/1995/September/Day-12/pr-25.html.
International Search Report International Application; Serial No. PCT/GB02/01986; 6 pgs.
Webb et al., "Daptomycin Eluted from Calcium Sulfate Appears Effective Against *Staphylococcus*", Symposium: Papers Presented at the 2007 Meeting of the Musculoskeletal Infection Society, The Association of Bone and Joint Surgeons, 2008.

* cited by examiner

*Primary Examiner* — Carlos Azpuru
*Assistant Examiner* — Casey Hagopian
(74) *Attorney, Agent, or Firm* — Tarolli, Sundheim, Covell & Tummino LLP

(57) ABSTRACT

A bone graft composition includes beta-tricalcium phosphate and calcium sulphate and slowly soluble sources of calcium ions and hydroxyl ions.

16 Claims, No Drawings

CALCIUM PHOSPHATE/SULFATE-BASED BONE IMPLANT COMPOSITION

RELATED APPLICATIONS

This application is a continuation-in-part of U.S. patent application Ser. No. 12/356,357, filed Jan. 20, 2009, which is a currently-pending divisional of U.S. patent application Ser. No. 10/476,242, filed Mar. 25, 2004, filed as Application No. PCT/GB02/01986 on May 1, 2002, which claims priority to GB0110726.7, filed May 2, 2001. All of the above-identified applications, from which priority is claimed, are incorporated herein by reference in their entireties for all purposes.

FIELD OF THE INVENTION

This invention concerns a bone implant composition, containing a therapeutic agent, and a method of mixing to form a bone graft.

BACKGROUND

In orthopedic and dental surgical applications there is a great need for biocompatible and bioresorbable implant material which can be conveniently and effectively used as a bone substitute. This includes bone lost due to periodontal disease, ridge augmentation, sinus elevation, bone defects or cavities due to trauma, disease or surgery and spinal fusions. Following implantation the bone substitute is ideally resorbed in a time frame which is consistent with its replacement by new vital bone.

The bone graft material of preferred choice is autograft, i.e. the patient's own bone, since this is totally biocompatible, is not subject to an immune response or disease transmission and has good osteogenic capacity. However, its source is limited, it requires a second surgical procedure for harvest and there are often donor site morbidity problems.

Allograft bone is usually considered an acceptable alternative since it is more readily available and has a reasonable level of efficacy. However, it has the potential for disease transmission and since it is 'foreign' tissue there is the potential for immunological reactions. In addition, it is a material variable in its properties, due to donor source (often elderly people with osteoporotic bones) and processing variability. This makes prediction of clinical outcome difficult when allograft is used. Delayed healing is a frequent complication.

Calcium sulphate and calcium phosphate bone cements consist of a powder and an aqueous liquid component. Mixing of these components gives a material having a paste consistency and results in a chemical hydration reaction leading to stiffening and setting of the mixture as the reaction proceeds to completion. It is increasingly required in many surgical procedures to add therapeutic agents to the bone cement to deliver the agent to the surgical site. This is often the case in cases of bone infection where the presence of locally delivered antibiotic or antifungal agents can have significant advantages compared to the traditional oral or parenteral delivery route. These therapeutically active materials are added to the cement when the powder and liquid components are mixed together. As such they then become homogeneously incorporated and uniformly distributed throughout the set/cured cement.

Multi-drug resistant (MDR) bacterial strains are now widespread in all hospitals. Increasingly high doses of antibiotics are needed in order to provide concentration levels which exceed the minimum inhibitory concentration (MIC) required to effectively kill all bacteria. If administered intravenously this increases the potential for systemic toxicity effects, in addition to further increasing the potential for bacterial resistance. It is being increasingly recognised that the delivery of the antibiotic directly to the contaminated site is the best way to exceed the MIC while limiting systemic toxicity effects. Poly-methyl methacrylate (PMMA) cement is often used as a carrier for antibiotic delivery. It does have, however, a number of disadvantages. It cures at a relatively high temperature, over 80° C. for sections thicker than a few millimeters, and many antibiotics are not thermally stable at these temperatures. It is a non-resorbing material and as such the beads must be removed in a second surgical procedure following eradication of the infection. Because of the non-resorbing nature of the PMMA much of the antibiotic that is mixed with the material is 'locked in' and only a small proportion is eluted. For these reasons, calcium sulphate and calcium phosphate bone cements are being used as carriers for the local delivery of antibiotics and other therapeutically active materials.

Identification of the type of bacterial contamination is essential. The surgeon will choose the appropriate antibiotic or antifungal for the type of pathogen involved. It is often advantageous to use a combination of two or more antibiotics to ensure satisfactory killing efficiency. The antibiotics are thoroughly mixed with the bone cement at the time of surgery. The mixture can be cast into a suitable mould where it is allowed to cure or set or simply administered to the surgical site and allowed to cure in situ. Following hardening the pellets can be removed from the mould by flexing the mould. To allow this flexing the mould is made from a flexible polymer such as a silicone resin.

Many therapeutic agents including antibiotics, antifungals, antivirals, NSAIDs and proteins or proteinacious material can have a significant effect on the setting time of bioactive (calcium sulphate and calcium phosphate) bone cements. Some materials will retard the setting process while others will inhibit setting completely. When mixed at the time of surgery it is important for these mixtures to set in a time frame consistent with the timing of the procedure, typically within the range of a few up to about 20 minutes. This will enable the surgical team to prepare the bone cement pellets, allowing them to harden, and implant them at the time of surgery.

There is thus a requirement for a method to ensure that therapeutic agents which retard or inhibit setting can be added to a bioactive bone cement mixture which subsequently sets within this time frame.

DETAILED DESCRIPTION

According to the present invention there is provided a bone cement composition, the composition comprising calcium sulphate and slowly soluble sources of calcium, orthophosphate and hydroxyl ions incorporating a therapeutic agent and a method of mixing said cement.

The source of the ions is preferably provided by compounds which are slowly soluble in water, and preferably compounds where the water solubility at room temperature is less than 5 g per litre, desirably less than 1 g per litre, and more desirably less than 0.1 g per litre.

The source of the calcium ions may be the calcium sulphate alone, or may be provided by one or more of: calcium carbonate, calcium phosphate, calcium oxide, calcium fluoride, calcium citrate, calcium stearate, or dolomite.

The calcium sulphate may be in the form of dihydrate, hemi-hydrate, soluble anhydrite or insoluble anhydrite. The ratio of calcium sulphate to all other compounds in the composition is preferably between 0.2 and 2 parts by weight.

The composition may also comprise a medicament, and desirably in an effective therapeutic amount. The medicament may comprise any of: an antibiotic, an antifungal, an antiviral, an anti-cancer agent, or bone morphogenic protein.

It may be advantageous to incorporate in the bone cement composition a material which accelerates the setting reaction, typically known as an accelerant. The accelerants may be, but are not limited to potassium sulphate, sodium sulphate or sodium chloride. The presence of an accelerant is able to significantly reduce the cure times of the bone graft cement composition, by amounts from 30% or more, or even greater than 50%.

The source of orthophosphate ions may be one or more of: hydroxyapatite, alpha tricalcium phosphate, beta tricalcium phosphate, dicalcium phosphate, tetracalcium phosphate or magnesium orthophosphate. The source of orthophosphate ions may be in the form of a micro-porous granular solid. The granules may have a particle size in the range 0.2-5.00 mm. The source of orthophosphate may be in the form of a microporous granular solid component.

The source of the hydroxyl ions may be one or more of: calcium oxide, insoluble anhydrite, calcium hydroxide, magnesium oxide, magnesium hydroxide, zinc oxide, zinc hydroxide, or basic magnesium carbonate.

In the composition the ratio of basicity to orthophosphate is preferably between 0.0 and 1.0 molar.

The composition may be in the form of a powder which can be mixed with water or an aqueous solution to form a usable paste.

Alternatively, the composition may be in the form of granules or pellets. The composition may be formed into pellets using a tablet press.

The invention also provides a method of forming a bone graft, the method comprising using a bone implant composition according to any of the preceding ten paragraphs.

When in powder form the composition may be mixed with water or an aqueous solution to form a putty or paste prior to application. The putty or paste may be applied to a surgical site by a suitable applicator such as a syringe. Alternatively the putty or paste may be applied to a mould and allowed to set prior to presentation to the surgical site.

Where the composition is in the form of granules or pellets, the granules or pellets can be packed into a bone cavity or soft tissue site.

According to a further embodiment of the invention, there is provided a method of forming a bone graft cement containing a clinically effective quantity of a therapeutic agent; the method comprising pre-mixing the cement composition for a first period of time prior to the addition of the therapeutic agent, adding the therapeutic agent and mixing for a second period of time then allowing the mixture to hydrate and set undisturbed.

This pre-mixing step prior to the addition of the antibiotic results in a significant reduction in cure times in comparison with the standard mixing of the bone graft cement which does not include the pre-mixing step prior to the addition of the antibiotic. Cure time reductions of greater than 60%, and in some cases even greater than 90%, are observed.

The first period of time may be in the range of from 15 seconds to 2 minutes, while the second period of time may be in the range 10 seconds to 1 minute.

The method may also include the addition of an accelerant, such as, but not limited to, one or more selected from the group consisting of potassium sulphate, sodium sulphate or sodium chloride. The addition of an accelerant is able to reduce the cure times still further, by at least 30% in many cases relative to when an accelerant is not employed, sometimes even greater than 50%.

The therapeutic agent used to make the bone graft cement may be either in a powdered or liquid form.

The therapeutic agent may also have the ability to retard or inhibit the setting of the bone graft cement. Typically, the therapeutic agent is selected from the group consisting of an antibiotic, an antifungal agent, an antiviral, a bone morphogenetic protein or NSAID, alone or in combination.

If it is desired to shape the bone graft cement into a pellet form, then, following the second period of mixing, the mixture may be pasted into a pellet mould before being allowed to hydrate and set undisturbed, to form pellets of the bone graft cement.

According to a further embodiment of the invention, there is provided a method of treating an infection in a soft tissue site by applying the bone graft cement pellets, and packing one or more of the said pellets into a soft tissue site.

Embodiments of the present invention will now be described by way of example only.

EXAMPLE 1

A powdered mixture was prepared according to the following composition:—
 1.25 g beta tricalcium phosphate
 0.63 g calcium sulphate alpha hemihydrate
 0.05 g magnesium oxide
 The beta tricalcium phosphate particles have a size of 250-500 microns.

The mixture was blended with 0.85 ml of a 1% potassium sulphate solution to give a paste which was used to fill a periodontal pocket.

EXAMPLE 2

A powdered mixture was prepared according to the following composition:—
 35.0 g beta tricalcium phosphate granules with a particle size of 1-2 mm diameter.
 17.5 g calcium sulphate dihydrate
 2.2 g magnesium oxide
 0.80 g calcium stearate
 The mixture was pressed into pellets 3 mm diameter by 2.5 mm deep using a tablet press. The pellets were used to fill a bone cavity.

EXAMPLE 3

A powdered mixture was prepared according to the following composition:—
 35.0 g alpha tricalcium phosphate
 14.0 g anhydrous calcium sulphate-insoluble form
 10.0 g basic magnesium carbonate
 0.1 g zinc oxide
 The mixture was pressed into pellets using a tablet press.

EXAMPLE 4

A powdered mixture was prepared according to the following composition:—
 10.0 g beta tricalcium phosphate particles
 5.0 g calcium sulphate alpha hemihydrate powder
 0.5 g magnesium oxide
 The beta tricalcium phosphate particles have a size range of 1-2 mm.

The mixture was blended with 9.5 ml of water and compacted into 6 mm diameter cylindrical moulds where it was allowed to set. The set pellets were removed from the moulds and allowed to dry. These were used to fill a bone cavity.

Pellets were prepared according to Example 4 but contained a non-steroidal anti-inflammatory and were implanted in soft tissue.

EXAMPLE 5

A powdered mixture was prepared according to the previous example (Example 4), but including 5% by weight of the antibiotic gentamycin which was added to the powdered mix prior to moulding.

There is thus described a bone implant composition and a method of using same which provides for considerable advantages. The composition is based upon the following chemical equation:—

$$10Ca^{2+} + 6PO_4^{3-} + 2OH^- \rightarrow Ca_{10}(PO_4)_6(OH)_2$$

The composition provides a source of ions which precipitate in vivo to provide a poorly crystalline, substituted apatite which closely mimics the natural mineral phase of bone (often described as 'bone-like-apatite'), in contrast to other presently available synthetic bone graft substitutes. Also, the reaction occurs over a time frame commensurate with the body's ability to regenerate new healthy bone. This precipitated hydroxyapatite is amenable to osteoclastic resorption. The calcium sulphate phase initially present resorbs by a simple dissolution mechanism over a period of a few weeks to provide a macroporous structure amenable to vascularisation and invasion by new bony tissue. The calcium sulphate forms a micro-porous barrier which prevents intrusion of unwanted soft tissue (cells) in the immediate post implantation period.

The source of ortho phosphate is preferably a micro-porous granular solid, with a particle size of 0.2-5 mm. This size range provides for an intergranule pore size of 100-200 microns which is necessary for cell infiltration and vascularization to stimulate new bone in-growth.

Various modifications may be made without departing from the scope of the invention. The calcium ions may be obtained from the calcium sulphate alone, or may also be obtained from calcium stearate as in Example 2, or other calcium compounds such as calcium carbonate, calcium phosphate, calcium oxide, calcium fluoride, calcium citrate or dolomite. In addition or as an alternative to the orthophosphate ions being provided by beta tricalcium phosphate, these ions may be provided by hydroxyapatite, alpha tricalcium phosphate, dicalcium phosphate, tetracalcium phosphate or magnesium orthophosphate. The composition may incorporate accelerants, retarders, plasticizers or viscosity modifiers.

In the examples the source of hydroxyl ions is magnesium oxide, and also zinc oxide in Example 3. These ions may though additionally or as an alternative be obtained from calcium oxide, insoluble anhydrite, calcium hydroxide, magnesium hydroxide, zinc hydroxide or basic magnesium carbonate. As illustrated in the Examples, the calcium sulphate may be in one or more of the following forms:—alpha hemihydrate, beta hemihydrate, soluble anhydrite, insoluble anhydrite or dihydrate.

The composition may comprise a medicament in an effective therapeutic amount, which medicament may comprise an antibiotic, an antifungal, an antiviral, an anti-cancer agent, or bone morphogenic protein.

Whilst endeavouring in the foregoing specification to draw attention to those features of the invention believed to be of particular importance it should be understood that the Applicant claims protection in respect of any patentable feature or combination of features hereinbefore referred to and/or shown in any drawings whether or not particular emphasis has been placed thereon.

EXAMPLE 6

A powdered mixture was prepared according to the following composition:—

10.0 g beta tricalcium phosphate
10.0 g calcium sulphate alpha hemihydrate
0.1 g magnesium oxide
0.2 g potassium sulphate (as a setting accelerant)
1.0 g powdered Daptomycin The mixture was blended with 6 ml of sterile water and stirred for approximately 1 minute and then allowed to cure/set undisturbed, in an airtight container to prevent evaporative loss of hydrant. At 24 hours post-mixing the mixture was still soft having a consistency of toothpaste. The presence of the Daptomycin had inhibited hydration and setting of the mixture.

According to the disclosure of the present invention, a similar mixture was prepared without the Daptomycin being present. The mixture was blended with 6 ml of sterile water and stirred for approximately 1 minute and then the Daptomycin powder (1.0 g) was added. The mixture was continued to be stirred for a further 30 seconds before being allowed to cure/set undisturbed. At 17 minutes post-mixing the mixture had firmed, solidified and set.

Other antibiotics and antifungals which are known to retard/inhibit the setting of calcium sulphate based bone cements include but is not limited to: Amikacin, Ciprofloxacin, Meropenam, Tobramycin, Amphotericin B, Piperacillin, Tazobactam, Ceftriaxone, Bactrim, Zyvox, Clindamycin, Rifampin.

EXAMPLE 7

A powdered mixture was prepared according to the following composition:—

10.0 g beta tricalcium phosphate particles
5.0 g calcium sulphate alpha hemihydrate powder
0.5 g magnesium oxide
0.5 g Indomethacin The beta tricalcium phosphate particles have a size range of 1-2 mm.

The mixture was blended with 9.5 ml of water and compacted into 4 mm diameter cylindrical moulds where it was allowed to set. The set pellets were removed from the moulds following hardening/curing and subsequently used to fill soft tissue defects in order to inhibit heterotopic ossification following extremity war injuries.

EXAMPLE 8

Mixing Table

| Antibiotic | Form | Dosage | Liquid | Mixing Time/Technique | Set Time Standard Cure (with accelerant) HH:MM:SS | Standard Cure (without accelerant) HH:MM:SS |
|---|---|---|---|---|---|---|
| Ciprofloxacin | Powder | 1000 mg | 6 ml | mix with cement for 30 seconds | >02:00:00 | >02:00:00 |
| Ciprofloxacin | Powder | 1000 mg | 6 ml | pre-mix for 1 min then add ABX. Stir for 30 seconds | 00:07:44 | 00:12:30 |
| Daptomycin | Powder | 1000 mg | 6 ml | mix with cement for 30 seconds | >02:00:00 | >02:00:00 |
| Daptomycin | Powder | 1000 mg | 6 ml | pre-mix for 1 min then add ABX. Stir for 30 seconds | 00:17:32 | 00:28:23 |
| Tobramycin | Powder | 1000 mg | 6 ml | mix with cement for 30 seconds | 00:53:26 | >02:00:00 |
| Tobramycin | Powder | 1000 mg | 6 ml | pre-mix for 1 min then add ABX. Stir for 30 seconds | 00:06:43 | 00:09:05 |

ABX = Antibiotic
HH = Hour(s)
MM = Minute(s)
SS = Second(s)

It can thus also be seen that the samples which include the pre-mixing step prior to the addition of the antibiotic cause a significant reduction in the cure times in comparison with the standard mixing of the bone graft cement which does not include the pre-mixing step prior to the addition of the antibiotic. A reduction in cure time of from greater than 2 hours down to under half an hour, and even as low as under 10 minutes, is observed.

It can also be seen that the samples which include the accelerant in combination with the cement and antibiotic exhibit significantly reduced cure times relative to the samples which do not contain the accelerant—from 12.5 minutes to 7.75 minutes, or from over 28 minutes down to 17.5 minutes, or from greater than 2 hours to under 53.5 minutes, or from over 9 minutes to under 7. The cure time is thus reduced by at least 30% in many cases, sometimes even greater than 50%.

There is thus disclosed a method to enable a bone cement mixture to be blended with an antibiotic, antifungal or other therapeutic agent which normally would retard or inhibit setting, such that the mixture proceeds to hydrate and fully set hard in an acceptable time period.

Having described the invention, the following is claimed:

1. A method of forming a bone graft cement wherein the cement composition comprises beta-tricalcium phosphate and calcium sulfate and slowly soluble sources of calcium ions, hydroxyl ions and an aqueous solution; containing a clinically effective quantity of a therapeutic agent; the method comprising pre-mixing the cement composition for a first period of time prior to the addition of the therapeutic agent, adding the therapeutic agent and mixing for a second period of time then allowing the mixture to hydrate and set undisturbed.

2. A method of forming a bone graft cement according to claim 1, further comprising adding an accelerant.

3. A method of forming a bone graft cement according to claim 2, wherein the accelerant is selected from the group consisting of potassium sulphate, sodium sulphate or sodium chloride.

4. A method of forming a bone graft cement according to claim 1 where the therapeutic agent is in a powdered or liquid form.

5. A method of forming a bone graft cement according to claim 1 where, following the second period of mixing, the mixture is pasted into a pellet mould before being allowed to hydrate and set undisturbed, to form pellets of the bone graft cement.

6. A method of forming a bone graft cement according to claim 1 where the first period of time is in the range of 15 seconds to 2 minutes.

7. A method of forming a bone graft cement according to claim 1 where the second period of time is in the range of 10 seconds to 1 minute.

8. A method of forming a bone graft cement according to claim 1 where the therapeutic agent is one that is able to retard or inhibit the setting of the bone graft cement.

9. A method of forming a bone graft cement according to claim 8 where the therapeutic agent is selected from the group consisting of an antibiotic, an antifungal agent, an antiviral, a bone morphogenetic protein or NSAID, alone or in combination.

10. A method of forming a bone graft cement according to claim 1 wherein the beta-tricalcium phosphate is in the form of granules.

11. A method of forming a bone graft cement according to claim 10, wherein the beta-tricalcium phosphate granules have a particle size in the range of 0.4-5.0 mm.

12. A method of forming a bone graft cement according to claim 1 wherein the calcium sulphate is selected from the group consisting of dihydrate, hemi-hydrate, soluble anhydrite and insoluble anhydrite.

13. A method of forming a bone graft cement according to claim 1 wherein the source of ions are provided by compounds having a water solubility at room temperature of less than 5 grams per litre.

14. A method of forming a bone graft cement according to claim 1 wherein the source of ions are provided by compounds having a water solubility at room temperature of less than 1 gram per litre.

15. A method of forming a bone graft cement according to claim 1, wherein the cement composition forms a bone graft cement when mixed with water or a non-acidic aqueous solution.

16. A method of forming a bone graft cement according to claim 15 wherein the aqueous solution is either water or a non-acidic aqueous solution.

* * * * *